US005989821A

United States Patent [19]
Goh et al.

[11] Patent Number: 5,989,821
[45] Date of Patent: Nov. 23, 1999

[54] UNIVERSAL TARGETS FOR SPECIES IDENTIFICATION

[75] Inventors: Swee Han Goh, Vancouver; Anthony Chow, W. Vancouver; Sean Hemmingsen, Saskatoon, all of Canada

[73] Assignees: University of British Columbia, Vancouver, Canada; The National Research Council of Canada, Ottawa, Canada

[21] Appl. No.: 09/003,067

[22] Filed: Jan. 5, 1997

Related U.S. Application Data

[62] Division of application No. 08/429,121, Apr. 26, 1995, Pat. No. 5,708,160.

[51] Int. Cl.$^6$ .............. C12Q 1/68; C12P 19/34; C07H 21/02; C07H 21/04
[52] U.S. Cl. ................. 435/6; 435/5; 435/91.1; 435/91.2; 536/23.1; 536/24.3; 536/24.31; 536/24.32; 536/24.33
[58] Field of Search .................. 435/5, 6, 91.1, 435/91.2; 536/24.3, 24.31, 24.32, 24.33, 23.1

[56] References Cited

U.S. PATENT DOCUMENTS

| | | | |
|---|---|---|---|
| 5,232,833 | 8/1993 | Sanders et al. | 435/7.21 |
| 5,464,750 | 11/1995 | Sanders et al. | 435/7.21 |
| 5,494,796 | 2/1996 | Spears et al. | 435/6 |

FOREIGN PATENT DOCUMENTS

| | | |
|---|---|---|
| A-0468520 | 1/1992 | European Pat. Off. |
| A-9207874 | 5/1992 | WIPO. |

OTHER PUBLICATIONS

Perkin Elmer Cetus Geneamp DNA amplification reagent kit instructions (1990).
Sipos et al., "Cloning and sequencing of the gene coding for the 10–and 60–kDa heat shock proteins from Pseudomonas aeruginosa and mapping of a species specific epitope", Inf. Immun. 59(9):3219–3226 (1991).
Ohta et al., "Molecular characterization of the gene operon of heat shock proteins HSP60 and HSP10 in methicillin resistant staphlococcus aureus", Biochem. Biophys. Res. Comm. 193(2):730–737 (1993).
Hemmingsen et al., "Homologous plant and bacterial proteins chaperone oligomeric protein assembly", Nature 333:330–334 (1988).
Plikaytis et al., "Differentiation of Slowly Growing Myobacterium Species, Including Myobacterium tuberculosis, by Gene Amplification and Restriction Fragment Length Polymorphism Analysis", *Journal of Clinical Microbiology*, vol. 30, No. 7, pp. 1815–1822 (Jul. 1, 1992).
Telenti et al., "Rapid Identification of Mycobacterium to the Species Level by Polymerase Chain Reaction and Restriction Enzyme Analysis", *Journal of Clinical Microbiology*, vol. 31, No. 2, pp. 175–178, Feb. 1, 1993.
Octavian Lungu et al., "Differentiation of Nocardia from Rapidly Growing Mycobacterium Species by PCR–RFLP Analysis", *Diagn. Microbiol. Infect. Dis.*, vol. 18, pp. 13–18, Jan. 18, 1994.
Goh et al., "HSP60 Gene Sequences as Universal Targets for Microbial Species Identification Studies with Coagulase–Negative Staphylococci", *Journal of Clinical Microbiology*, vol. 34, No. 4, pp. 818–823, Apr. 1996.

*Primary Examiner*—Jeffrey Fredman
*Attorney, Agent, or Firm*—Fish & Richardson P.C.

[57] ABSTRACT

The present invention provides oligonucleotide primers and a method of using these primers for identification of the species of an organism, wherein the identification includes amplification of a variable polynucleotide sequence encoding a highly conserved region of a heat shock polypeptide.

7 Claims, 7 Drawing Sheets

```
Agrobacterium tumefaciens   X68263   ATGRCEOP
H279 5-GAC ATC GCC GGT GAC GGC ACC ACC AC-3 AT
H280 5-AAG GCT CCT GGC TTC GGC GAT CGC CG-3 AT Bacillus stearothermophilus   L10732   BACSGROESL
H279 5-GAT GTT GCT GGG GAC GGT ACA ACA AC-3 BSt
H280 5-AAA GCG CCT GGC TTC GGC GAT CGT CG-3 BSt Bacillus subtilis   D10972,D01157   BACGRCEL
H279 5-GAC GTT GCC GGT GAC GGT ACA ACA AC-3 BS
H280 5-AAA GCT CCT GGT TTC GGT GAT CGC CG-3 BS Bacteriodes gingivalis   X78435   ENRGRCES
H279 5-GAC GAT GCC GGT GAC GGT ACG ACT AC-3 BG
H280 5-AAG GCT CCC GGA TTC GGC GAT CGT CG-3 BG Bartonella bacilliformis Z15160   BBGROELT
H279 5-GAT ATT GCT GGT GAT GGA ACG ACA AC-3 BB
H280 5-AAA GCT CCA GGT TTT GGT GAC CGC CG-3 BB Borrelia burgdorferi   X65139   BBHSP60
H279 5-GAT GTT GCT GGT GAT GGA ACA ACA AC-3 Bbur
H280 5-AAA TCT CCT GGT TTT GGT GAT AGA CG-3 Bbur Bradyrhizobium japonicum Z22603   BJGROES3A
H279 5-GAT GCT GCT GGC GAC GGT ACC ACC AC-3 BJ
H280 5-AAG GCT CCG GGC TTC GGC GAT CGC CG-3 BJ Brucella abortus  M83930   BRIXTRO
H279 5-GAT ACT GCC GGT GAC GGC ACC ACG AC-3 BA
H280 5-AAG CGT CCG GGC TTC GGC GAT CGC CG-3 BA Chlamydia trachomatis   M58027   CHIGROE
H279 5-GAC AAA GCT GGA GAC GGA ACT ACA AC-3 CT
H280 5-AAA GCT CCA GGC TTT GGA GAT AGA AC-3 CT Chlamydia pneumoniae   M69217   CHTGRO
H279 5-GAC AAA GCA GGC GAC GGA ACT ACA AC-3 CP
H280 5-AAA CCT CCT GGT TTC GGT GAC AGA AG-3 CP Chlamydia psittaci   X51404 M25101   CPHYPAB
H279 5-GAT AAA GCT GGT GAT GGA ACT ACA AC-3 CPs
H280 5-AAA GCT CCT GGA TTT GGT GAT AGA AG-3 CPs Chromalium vinosum   M99443   CVNGROESLA
H279 5-GAC ATC GCC GGT GAC GGC ACC ACC AC-3 CV
H280 5-AAG GCG CCG GGC TTC GGT GAT CGT CG-3 CV Clostridium acetobutylicum   M74572   CLOGROESLA
H279 5-GAT GTA GCA GGA GAC GGA ACT ACT AC-3 CA
H280 5-AAA GCT CCT GGA TTT GGC GAT AGA AG-3 CA
```

FIG. 1A

Clostridium perfringens    X62914    CPGROESL
H279 5-GAT GTG GCA GGA GAT GGA ACT ACT AC-3 CPe
H280 5-AAA GCA CCT GGA TTT GGT GAT AGA AA-3 CPe Coxiella burnetii    M20482    CCXHSPAB
H279 5-GAC GAT GCG GGT GAT GGT ACC ACA AC-3 C3
H280 5-AAA GCA CCT GGC TTT GGC GAT CGT CG-3 C3

Ehrlichia chaffeensis    L10917    EHRHSP
H279 5-GAT AAA GTT GGT GAT GGA ACA ACT AC-3 ECh
H280 5-AAA GCG CCA GGG TTT GGT GAT AGA AG-3 ECh Escherichia coli    X07850    ECGRCEST
H279 5-GAC GCT GCA CGC GAC GGT ACC ACC AC-3 EC
H280 5-AAA GCA CCG GGC TTC GGC GAT CGT CG-3 EC Haemophilus ducreyi    M91030    HEAGRCESL
H279 5-GAT GTA GCT GGT GAT GGT ACA ACA AC-3 HD
H280 5-AAA GCA CCG GGC TTC GGC GAC CGT CG-3 HD Helicobacter pylori    X73840    HPHSP60
H279 5-GAT GCT GCC GGC GAT GGC ACG ACC AC-3 HP
H280 5-AAA GCT CCA CCC TTT GGG GAC AGA AG-3 HP Lactobacillus lactis    X71132    LLGRCESEL
H279 5-GAT ATC GCA GGT GAC GGT ACA AAC AC-3 LL
H280 5-AAA GCA CCA GGA TTT GGT GAT CGT CG-3 LL Legionella micdadei    X57520    LMGROELSR
H279 5-GAT ACC GCA GGT GAT GGT ACT ACT AC-3 LM
H280 5-AAA GCA CCT GGT TTC GGT GAT CGT CG-3 LM Legionella pneumophila    M91673 M35149    LPNHTPB
H279 5-GAT ACT GCT GGT GAT GGT ACT ACT AC-3 LP
H280 5-AAA GCG CCT GGT TTT GGT GAT CGC CG-3 LP Mycobacterium bovis    M17705    MSGROG
H279 5-GAC GTC GCC GGT GAC GGC ACC ACG AC-3 MB
H280 5-AAG GCT CCC GGC TTC GGC GAC CGC CG-3 MB Mycobacterium leprae    Z11665    MCGROEID
H279 5-GAC GTC GCT GGC GAC GGC ACT ACC AC-3 ML
H280 5-AAG TCC CCG TTC TTC GGC GAC CGA CG-3 ML Mycobacterium paratuberculosis    X74518    MPHSP65
H279 5-GAC GTC GCC GGT GAC GGC ACG ACG AC-3 MP
H280 5-AAG GCG CCC CCC TTC GGC GAC CGC CG-3 MP Mycobacterium tuberculosis    X60350    MTGROEOP
H279 5-GAT GTG GCC GGT GAC GGC ACC ACC AC-3 MT
H280 5-AAG GGG CCG TAC TTC GGT GAC CGC CG-3 MT

FIG. 1B

```
Neisseria meningitidis      Z22956      NMHSP63A
H279 5-GAC GTG GCG GGC GAC GGT ACG ACT AC-3 NM
H280 5-AAA GCT CCG GGC TTC GGC GAC CGC CG-3 NM Neisseria gonorrheae        Z23009      NGHSP63B
H279 5-GAC GTA GCC GGC GAC GGT ACG ACT AC-3 NG
H280 5-AAA GCC CCG GGC TTC GGC GAC CGC CG-3 NG Neisseria flavescens        Z22955      NFHSP63A
H279 5-GAC GTA GCC GGC GAC GGT ACC ACT AC-3 NF
H280 5-AAA GCC CCG GGC TTC GGC GAC CGC CG-3 NF Porphyromonas gingivalis D17398      POYPGGROE
H279 5-CAC GAT GCC GGT GAC GGT ACG ACT AC-3 PG
H280 5-AAG GCT CCC GGA TTC GGC GAT CGT CG-3 PG Pseudomonas aeruginosa      M63957      PSEGRCESL
H279 5-GAC GCT GCC GGT GAC GGC ACC ACC AC-3 PA
H280 5-AAG GCT CCG GGC TTC GGC GAT CGC CG-3 PA Pseudomonas putida   X78435      PPGRCESL
H279 5-GAT GCA GCC GGT GAC GGC ACC ACC AC-3 PP
H280 5-AAG CCA CCG GGC TTC GGC GAC CGT CG-3 PP Rhizobium leguminosarum   L20775      RHMCPN60A
H279 5-GAC ATC GCC GGC GAC GGC ACC ACG AC-3 RL
H280 5-AAG GCG CCC GGC TTC GGC GAT CGC CG-3 RL Rhizobium meliloti   M94190      RHMGROELC
H279 5-GAC ATT GCC GGC GAC GGC ACC ACC AC-3 RM
H280 5-AAG GCC CCG GCC TTC GGC GAC CGT CG-3 RM Rickettsia tsutsugamushi M31887   RTRSTPSTA
H279 5-GAT GTG GCT GGT GAT GGT ACA ACT AC-3 RT
H280 5-AAG GCA CCT GGT TTT GGT GAT --- CG-3 RT Salmonella typhi     U01039      U01039
H279 5-GAC GCT GCA GGC GAC GGC ACC ACC AC-3 ST
H280 5-AAA GCA CCG GGC TTC GCC GAT CGT CG-3 ST
```

FIG. 1C

```
Staphylococcus aureus      D14711    STAHSP
H279 5-GAA ATT GCT GGT GAC GGT ACG ACA AC-3 SA
H280 5-AAG GCG CCT GGT TTC GGT GAT CGT CG-3 SA Staphylococcus epidermidis  U13618  SBU13618
H279 5-GAA ATC GCT GGG GAC GGT ACA ACT AC-3 SB
H280 5-AAA GCC CCA GGA TTT GGT GAT CGA CG-3 SB Streptomyces albus     M76657    STMGROELX
H279 5-GAC ATC GCG GGT GAC GGC ACC ACC AC-3 Salbus
H280 5-AAC GCG CCC GGC TTC GGT GAC CGC CG-3 Salbus Streptomyces coelicolor    X75206    SCGROEL
H279 5-GAC ATC GCG GGT GAC GGC ACC ACC AC-3 SC
H280 5-AAG GCC CCC GGC TTC GGC GAC CGC CG-3 SC Synechococcus sp.    M58751    SYOGROESL
H279 5-GAC GCA GCC GGT GAC GGC ACC ACC AC-3 Sco
H280 5-AAA GCG CCT GGT TTC GGC GAT CGC CG-3 Sco Synechocyotis sp. (subsp. PCC 6803)  D12677   SYOGROESL
H279 5-GAT GTG GCT GGG GAT GGT ACC ACC AC-3 Scy
H280 5-AAA GCC CCC GGC TTT GGC GAT CGC CG-3 Scy Yersinia enterolitica     X68526    YEHSP60
H279 5-GAC GCT GCG GGT GAC GGT ACC ACT AC-3 YE
H280 5-AAA GCA CCT GGT TTC GGC GAC CGT CG-3 YE Zymomonas mobilis    L11654    ZMOGROESLA
H279 5-GAT CTG GCT GGT GAT GGC ACC ACC AC-3 ZM
H280 5-AAG GCT CCT GGC TTT GGT GAT CGT CG-3 ZM
```

FIG. 1D

| Isolate no. | Identification | Strain | Hybridization results with HSP60 probe specific for: | | | | | |
|---|---|---|---|---|---|---|---|---|
| | | | S. epidermidis | S. aureus | S. haemolyticus | S. schleiferi | S. saprophyticus | S. lugdunensis |
| 1 | S. aureus | 8325-4 | − | + | − | − | − | − |
| 2 | S. aureus | ATCC 29213 | − | + | − | − | − | − |
| 3 | S. aureus | 8387 | − | + | − | − | − | − |
| 4 | S. aureus | SA8 | − | + | − | − | − | − |
| 5 | S. aureus | ATCC 12600[a] | − | + | − | − | − | − |
| 6 | S. epidermidis | 9759 | + | − | − | − | − | − |
| 7 | S. epidermidis | ATCC 14990[a] | + | − | − | − | − | − |
| 8 | S. epidermidis | 8469 | + | − | − | − | − | − |
| 9 | S. epidermidis | 8331 | + | − | − | − | − | − |
| 10 | S. haemolyticus | ATCC 29970[a] | − | − | + | − | − | − |
| 11 | S. haemolyticus | 8459 | − | − | + | − | − | − |
| 12 | S. haemolyticus | 8564 | − | − | + | − | − | − |
| 13 | S. haemolyticus | 8589 | + | − | − | − | − | − |
| 14 | P. aeruginosa | ATCC 27853 | − | − | − | − | − | − |
| 15 | S. saprophyticus | 8523 | − | − | − | − | + | − |
| 16 | S. saprophyticus | 8524 | − | − | − | − | + | − |
| 17 | S. saprophyticus | 8638 | − | − | − | − | + | − |
| 18 | S. saprophyticus | 9761 | − | − | − | − | − | − |
| 19 | S. lugdunensis | CRSN 850412[a] | − | − | − | − | − | + |
| 20 | S. schleiferi | ATCC43808[a] | − | − | − | + | − | − |
| 21 | S. schleiferi | BOSTON[a] | − | − | − | + | − | − |
| 22 | S. capitis subsp. ureolyticus | ATCC 49326[a] | − | − | − | − | − | − |
| 23 | S. capitis subsp. capitis | ATCC 27840[a] | − | − | − | − | − | − |
| 24 | S. capitis | 8468 | + | − | − | − | − | − |
| 25 | S. hominis | ATCC 27844[a] | − | − | + | − | − | + |
| 26 | S. hominis | 9998 | − | − | − | − | − | − |
| 27 | S. hominis | 8458 | − | − | − | − | − | − |
| 28 | S. warneri | ATCC 27836[a] | − | − | − | − | − | − |
| 29 | S. warneri | 9290 | − | − | − | − | − | − |
| 30 | S. warneri | 8586 | − | − | − | − | − | − |

FIG. 4A

| Isolate no. | Identification | Strain | Hybridization results with HSP60 probe specific for: | | | | | |
|---|---|---|---|---|---|---|---|---|
| | | | S. epidermidis | S. aureus | S. haemolyticus | S. schleiferi | S. saprophyticus | S. lugdunensis |
| 31 | S. xylosus | ATCC 29971[a] | – | – | – | – | – | – |
| 32 | S. xylosus | 8584 | – | – | – | – | – | + |
| 33 | S. sciuri | ATCC 29061[a] | – | – | – | – | – | – |
| 34 | S. sciuri | 10034 | – | + | – | – | – | – |
| 35 | S. simulans | ATCC 27848[a] | – | – | – | – | – | – |
| 36 | E. coli | ATCC 25922 | – | – | – | – | – | – |
| 37 | S. simulans | 9852 | – | – | – | – | – | – |
| 38 | S. caprae | ATCC 35538[a] | – | – | – | – | – | – |
| 39 | S. auricularis | ATCC 33753[a] | – | – | – | – | – | – |
| 40 | S. cohnii subsp. cohnii | ATCC 29974[a] | – | – | – | – | – | – |
| 41 | S. capitis subsp. ureolyticus | ATCC 49325[a] | – | – | – | – | – | – |
| 42 | S. kloosii | ATCC 43959[a] | – | – | – | – | – | – |
| 43 | S. equorum | ATCC 43958[a] | – | – | – | – | – | – |
| 44 | S. arlettae | ATCC 43957[a] | – | – | – | – | – | – |
| 45 | S. carnosus | MA[a] | – | – | – | – | – | – |
| 46 | S. intermedius | CFDD[a] | – | – | – | – | – | – |
| 47 | S. delphini | Heidy[a] | – | – | – | – | – | – |
| 48 | S. hyicus | ATCC 11249[a] | – | – | – | – | – | – |
| 49 | S. chromogenes | CDC 2[a] | – | – | – | – | – | – |
| 50 | S. caseolyticus | ATCC 13548[a] | – | – | – | – | – | – |
| 51 | S. lentus | K20[a] | – | – | – | – | – | – |
| 52 | S. vitulus | ATCC 51145[a] | – | – | – | – | – | – |
| 53 | S. pasteuri | BM 10426[a] | – | – | – | – | – | – |
| 54 | S. gallinarum | ATCC 35539[a] | – | – | – | – | – | – |
| 55 | S. felis | GD 521[a] | – | – | – | – | – | – |
| 56 | S. schleiferi subsp. coagulans | ATCC 49545[a] | – | – | – | + | – | – |
| 57 | S. aureus | 7162 | – | + | – | – | – | – |
| 58 | B. subtilis | ATCC 12432 | – | – | – | – | – | – |
| 59 | 0.4 M NaOH | | | | | | | |

[a] Isolates kindly provided by W. Kloos, North Carolina St. University, Raleigh.

FIG. 4B 5,989,821

SEQUENCE LISTING (1) GENERAL INFORMATION:

(iii) NUMBER OF SEQUENCES: 94

(2) INFORMATION FOR SEQ ID NO:1:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

GTTGTCGTAC CRTCACCAGC AATTTC                                          26

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

AARGCGCCTG GTTTYGGTGA TMRNMR                                          26

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GANNNNGCNG GNGAYGGNAC NACNAC                                          26

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

YKNYKNTCNC CRAANCCNGG NGCYTT                                          26

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GACATCGCCG GTGACGGCAC CACCAC                                              26

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AAGGCTCCTG GCTTCGGCGA TCGCCG                                              26

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GATGTTGCTG GGGACGGTAC AACAAC                                              26

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

AAAGCGCCTG GCTTCGGCGA TCGTCG                                              26

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GACGTTGCCG GTGACGGTAC AACAAC                                              26

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

AAAGCTCCTG GTTTCGGTGA TCGCCG                                              26

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GACGATGCCG GTGACGGTAC GACTAC                                             26

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AAGGCTCCCG GATTCGGCGA TCGTCG                                             26

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GATATTGCTG GTGATGGAAC GACAAC                                             26

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

AAAGCTCCAG GTTTTGGTGA CCGCCG                                             26

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GATGTTGCTG GTGATGGAAC AACAAC                                             26

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

AAATCTCCTG GTTTTGGTGA TAGACG 26

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GATGCTGCTG GCGACGGTAC CACCAC 26

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

AAGGCTCCGG GCTTCGGCGA TCGCCG 26

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

GATACTGCCG GTGACGGCAC CACGAC 26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AAGCGTCCGG GCTTCGGCGA TCGCCG 26

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
GACAAAGCTG GAGACGGAAC TACAAC                                                  26

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

AAAGCTCCAG GCTTTGGAGA TAGAAC                                                  26

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GACAAAGCAG GCGACGGAAC TACAAC                                                  26

(2) INFORMATION FOR SEQ ID NO:24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

AAAGCTCCTG GTTTCGGTGA CAGAAG                                                  26

(2) INFORMATION FOR SEQ ID NO:25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GATAAAGCTG GTGATGGAAC TACAAC                                                  26

(2) INFORMATION FOR SEQ ID NO:26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

AAAGCTCCTG GATTTGGTGA TAGAAG                                                  26

(2) INFORMATION FOR SEQ ID NO:27:
```

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:27:

GACATCGCCG GTGACGGCAC CACCAC    26

(2) INFORMATION FOR SEQ ID NO:28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

AAGGCGCCGG GCTTCGGTGA TCGTCG    26

(2) INFORMATION FOR SEQ ID NO:29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

GATGTAGCAG GAGACGGAAC TACTAC    26

(2) INFORMATION FOR SEQ ID NO:30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

AAAGCTCCTG GATTTGGCGA TAGAAG    26

(2) INFORMATION FOR SEQ ID NO:31:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GATGTGGCAG GAGATGGAAC TACTAC    26

(2) INFORMATION FOR SEQ ID NO:32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

AAAGCACCTG GATTTGGTGA TAGAAA                                          26

(2) INFORMATION FOR SEQ ID NO:33:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:33:

GACGATGCGG GTGATGGTAC CACAAC                                          26

(2) INFORMATION FOR SEQ ID NO:34:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:34:

AAAGCACCTG GCTTTGGCGA TCGTCG                                          26

(2) INFORMATION FOR SEQ ID NO:35:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:35:

GATAAAGTTG GTGATGGAAC AACTAC                                          26

(2) INFORMATION FOR SEQ ID NO:36:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:36:

AAAGCGCCAG GGTTTGGTGA TAGAAG                                          26

(2) INFORMATION FOR SEQ ID NO:37:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:37:

```
GACGCTGCAG GCGACGGTAC CACCAC                                            26

(2) INFORMATION FOR SEQ ID NO:38:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:38:

AAAGCACCGG GCTTCGGCGA TCGTCG                                            26

(2) INFORMATION FOR SEQ ID NO:39:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:39:

GATGTAGCTG GTGATGGTAC AACAAC                                            26

(2) INFORMATION FOR SEQ ID NO:40:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:40:

AAAGCACCGG GCTTCGGCGA CCGTCG                                            26

(2) INFORMATION FOR SEQ ID NO:41:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:41:

GATGCTGCCG GCGATGGCAC GACCAC                                            26

(2) INFORMATION FOR SEQ ID NO:42:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:42:

AAAGCTCCAC CCTTTGGGGA CAGAAG                                            26

(2) INFORMATION FOR SEQ ID NO:43:
```

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:43:

GATATCGCAG GTGACGGTAC AAACAC                                               26

(2) INFORMATION FOR SEQ ID NO:44:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:44:

AAAGCACCAG GATTTGGTGA TCGTCG                                               26

(2) INFORMATION FOR SEQ ID NO:45:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:45:

GATACCGCAG GTGATGGTAC TACTAC                                               26

(2) INFORMATION FOR SEQ ID NO:46:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:46:

AAAGCACCTG GTTTCGGTGA TCGTCG                                               26

(2) INFORMATION FOR SEQ ID NO:47:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:47:

GATACTGCTG GTGATGGTAC TACTAC                                               26

(2) INFORMATION FOR SEQ ID NO:48:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:48:

AAAGCGCCTG GTTTTGGTGA TCGCCG                                              26

(2) INFORMATION FOR SEQ ID NO:49:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:49:

GACGTCGCCG GTGACGGCAC CACGAC                                              26

(2) INFORMATION FOR SEQ ID NO:50:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:50:

AAGGCTCCCG GCTTCGGCGA CCCGCCG                                             27

(2) INFORMATION FOR SEQ ID NO:51:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:51:

GACGTCGCTG GCGACGGCAC TACCAC                                              26

(2) INFORMATION FOR SEQ ID NO:52:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:52:

AAGTCCCCGT TCTTCGGCGA CCGACG                                              26

(2) INFORMATION FOR SEQ ID NO:53:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:53:

```
GACGTCGCCG GTGACGGCAC GACGAC                                              26

(2) INFORMATION FOR SEQ ID NO:54:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:54:

AAGGCGCCCC CCTTCGGCGA CCGCCG                                              26

(2) INFORMATION FOR SEQ ID NO:55:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:55:

GATGTGGCCG GTGACGGCAC CACCAC                                              26

(2) INFORMATION FOR SEQ ID NO:56:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:56:

AAGGGGCCGT ACTTCGGTGA CCGCCG                                              26

(2) INFORMATION FOR SEQ ID NO:57:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:57:

GACGTGGCGG GCGACGGTAC GACTAC                                              26

(2) INFORMATION FOR SEQ ID NO:58:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:58:

AAAGCTCCGG GCTTCGGCGA CCGCCG                                              26

(2) INFORMATION FOR SEQ ID NO:59:
```

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:59:

GACGTAGCCG GCGACGGTAC GACTAC                         26

(2) INFORMATION FOR SEQ ID NO:60:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:60:

AAAGCCCCCG GCTTCGGCGA CCGCCG                         26

(2) INFORMATION FOR SEQ ID NO:61:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:61:

GACGTAGCCG GCGACGGTAC CACTAC                         26

(2) INFORMATION FOR SEQ ID NO:62:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:62:

AAAGCCCCCG GCTTCGGCGA CCGCCG                         26

(2) INFORMATION FOR SEQ ID NO:63:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:63:

CACGATGCCG GTGACGGTAC GACTAC                         26

(2) INFORMATION FOR SEQ ID NO:64:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:64:

AAGGCTCCCG GATTCGGCGA TCGTCG 26

(2) INFORMATION FOR SEQ ID NO:65:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

GACGCTGCCG GTGACGGCAC CACCAC 26

(2) INFORMATION FOR SEQ ID NO:66:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:66:

AAGGCTCCGG GCTTCGGCGA TCGCCG 26

(2) INFORMATION FOR SEQ ID NO:67:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:67:

GATGCAGCCG GTGACGGCAC CACCAC 26

(2) INFORMATION FOR SEQ ID NO:68:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:68:

AAGCCACCGG GCTTCGGCGA CCGTCG 26

(2) INFORMATION FOR SEQ ID NO:69:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:69:

```
GACATCGCCG GCGACGGCAC CACGAC                                                26
```

(2) INFORMATION FOR SEQ ID NO:70:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

```
AAGGCGCCCG GCTTCGGCGA TCGCCG                                                26
```

(2) INFORMATION FOR SEQ ID NO:71:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:71:

```
GACATTGCCG GCGACGGCAC CACCAC                                                26
```

(2) INFORMATION FOR SEQ ID NO:72:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:72:

```
AAGGCCCCGG CCTTCGGCGA CCGTCG                                                26
```

(2) INFORMATION FOR SEQ ID NO:73:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:73:

```
GATGTGGCTG GTGATGGTAC AACTAC                                                26
```

(2) INFORMATION FOR SEQ ID NO:74:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:74:

```
AAGGCACCTG GTTTTGGTGA TCG                                                   23
```

(2) INFORMATION FOR SEQ ID NO:75:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:75:

GACGCTGCAG GCGACGGCAC CACCAC                                              26

(2) INFORMATION FOR SEQ ID NO:76:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:76:

AAAGCACCGG GCTTCGCCGA TCGTCG                                              26

(2) INFORMATION FOR SEQ ID NO:77:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:77:

GAAATTGCTG GTGACGGTAC GACAAC                                              26

(2) INFORMATION FOR SEQ ID NO:78:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:78:

AAGGCGCCTG GTTTCGGTGA TCGTCG                                              26

(2) INFORMATION FOR SEQ ID NO:79:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:79:

GAAATCGCTG GGGACGGTAC AACTAC                                              26

(2) INFORMATION FOR SEQ ID NO:80:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:80:

AAAGCCCCAG GATTTGGTGA TCGACG                                                        26

(2) INFORMATION FOR SEQ ID NO:81:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:81:

GACATCGCGG GTGACGGCAC CACCAC                                                        26

(2) INFORMATION FOR SEQ ID NO:82:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:82:

AACGCGCCCG GCTTCGGTGA CCGCCG                                                        26

(2) INFORMATION FOR SEQ ID NO:83:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:83:

GACATCGCGG GTGACGGCAC CACCAC                                                        26

(2) INFORMATION FOR SEQ ID NO:84:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:84:

AAGGCCCCCG GCTTCGGCGA CCGCCG                                                        26

(2) INFORMATION FOR SEQ ID NO:85:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:85:

```
GACGCAGCCG GTGACGGCAC CACCAC                                              26

(2) INFORMATION FOR SEQ ID NO:86:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:86:

AAAGCGCCTG GTTTCGGCGA TCGCCG                                              26

(2) INFORMATION FOR SEQ ID NO:87:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:87:

GATGTGGCTG GGGATGGTAC CACCAC                                              26

(2) INFORMATION FOR SEQ ID NO:88:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:88:

AAAGCCCCCG GCTTTGGCGA TCGCCG                                              26

(2) INFORMATION FOR SEQ ID NO:89:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:89:

GACGCTGCGG GTGACGGTAC CACTAC                                              26

(2) INFORMATION FOR SEQ ID NO:90:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:90:

AAAGCACCTG GTTTCGGCGA CCGTCG                                              26

(2) INFORMATION FOR SEQ ID NO:91:
```

```
    (i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:91:

GATCTGGCTG GTGATGGCAC CACCAC                                              26

(2) INFORMATION FOR SEQ ID NO:92:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:92:

AAGGCTCCTG GCTTTGGTGA TCGTCG                                              26

(2) INFORMATION FOR SEQ ID NO:93:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:93:

GTNGTNGTNC CAGTCNCCNG CNNNNTC                                             27

(2) INFORMATION FOR SEQ ID NO:94:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:94:

AAAGGCNCCN GGNTTTCGGN GANACAGNAC AG                                       32
```

UNIVERSAL TARGETS FOR SPECIES IDENTIFICATION

This is a divisional of U.S. application Ser. No. 08/429,121, filed Apr. 26, 1995, issuing Jan. 13, 1998 as U.S. Pat. No. 5,708,160.

BACKGROUND OF THE INVENTION

1. Field of the Invention

This invention relates generally to taxonomic and phylogenic identification of organisms and specifically to the use of universal oligonucleotide primers and HSP60 amplicons to identify and distinguish organisms at the species level.

2. Description of Related Art

Coagulase positive and negative Staphylococci such as *S. aureus* and *S. epidermidis* are clinically important human pathogens (Jarvis and Martinec, *J. Antimicrob. Chemother.*, 29(A):19–24, 1992; Kloos, and Lambe, Jr., *Amer. Society of Microbiology*, pp. 222–237, 1991). For example, coagulase negative Staphylococci are responsible for about 25% of nosocomial bacteremia in the United States (Banerjee, et al., *Am. J. Med.*, 3B:86–89 (Suppl.), 1991). Like other bacteria, these Staphylococci species respond to external stress agents by expressing a set of heat shock proteins (HSP) (Ellis and van der Vies, *Annu. Rev. Biochem.*, 60:321–347, 1991; Yura, et al., *Annu. Rev. Microbiol.*, 47:321–360, 1993; Qoronfleh, et al., *Antonie van Leeuwenhoek*, 58:79–86, 1990). Of the known molecular weight classes of HSPs, the 60 kD and 70 kD families have been the most studied with the GroEL gene product from *E. coli* (Hemmingsen, et al., *Nature*, 333:330–334, 1988) being representative of the 60 kD family. This protein functions as a molecular chaperone with Gro ES (HSP 10) by assisting in protein folding (Gething and Sambrook, *Nature*, 355:33–45, 1992; Craig, et al., *Cell*, 78:365–372, 1994; Martin, et al., *Nature*, 366:228–233, 1993).

Previously studied methods for Staphylococcal identification using PCR amplification of either the 16S rDNA genes (Greisen, et al., *J. Clin. Microbiol.*, 32:335–351, 1994) or spacer regions between 16S and 23S genetic loci as DNA targets (Jensen, et al., *Appl. Environ. Microbiol.*, 59:945–952, 1994) failed to differentiate unequivocally some of the Staphylococcal species tested. The most promising nucleic acid based method for identification of the Staphylococci has been developed mainly by El Solh and colleagues (De Buyser, et al., *J. Gen. Microbiol.*, 135:989–991, 1989; El Solh, et al., *VCH Publishers, Inc., N.Y.*, pp. 585–593, 1990; De Buyser, et al., *J. Gen. Microbiol.*, 138:889–899, 1992) and others (Thomson-Carter, et al., *J. Gen. Microbiol.*, 135:2093–2097, 1989; Bialkowska-Hobrzanska, et al., *Eur. J. Clin. Microbiol. Infect. Dis.*, 9:588–594, 1990; Pennington, et al., *J. Clin. Microbiol.*, 29:390–392, 1991). The method is based on Southern blot analyses of 16S rRNA gene polymorphisms following restriction enzyme digestion of genomic DNA and gel separation of the digested DNA. However, this method is deemed laborious and requires pure bacterial cultures.

Other non-nucleic acid based commercial identification kits for laboratory identification of Staphylococci are also currently available (e.g., API Staph-Trac, API 20GP and Vitek GPI). However, recent publications report shortcomings in these test kits, especially when used for the identification of coagulase negative staphylococci (Grant, et al., *Diagn. Microbiol. Infect. Dis.*, 18:1–5, 1994; Perl, et al., *Diagn. Microbiol. Infect. Dis.*, 18:151–155, 1994). Several commercial products are available for the identification of isolates from the central nervous system (CNS), to the species level, however, very few of these systems have been evaluated and challenged in a direct comparative fashion using appropriate reference methods.

Three studies have reported the use of various Mycobacterium genus specific primers to amplify various target regions of the HSP 65 genes of Mycobacteria via PCR (Hance, et al., *Mol. Microbiol.*, No. 3, 7:843–849, 1989; Plikaytis, et al., *J. Clin. Microbiol.*, 30:1815–1822, 1992; Telenti, et al., *J. Clin. Microbiol.*, 31:175–178, 1993). Hance, et al., used apparent species-specific complementary oligonucleotides to probe the PCR products. However, speciation was unsuccessful by this method.

Two other studies (Plikaytis, et al., supra; Telenti, et al., supra) described similar PCR strategies for Mycobacterial speciation, but these methods required the detection of restriction enzyme site polymorphisms (RFLP) within the PCR amplified products. Both methods relied on the use of two restriction enzymes for differentiating the Mycobacterial species. Also, intraspecies DNA RFLPs were observed. En initial studies with clinical samples (Telenti, et al., supra), problems were observed associated with generating sufficient PCR signals for visualizing DNA digestion products run on gels and with the presence of restriction enzyme inhibitors.

Consequently, there is an apparent need for a reliable and reproducible method for identifying and distinguishing Staphylococci species as well as other species of other genera. The present invention provides such a method.

SUMMARY OF THE INVENTION

The present invention is based on the discovery of a variable nucleic acid region of heat shock protein 60 (HSP60) genes, which can be used as a species specific target and/or probe for identification and classification of organisms. The identification of highly conserved regions flanking a variable region led to the production of universal primers which can be used to specifically amplify these variable regions of nucleic acid, thereby providing a target sequence for use as a probe and/or target to identify organisms. The discovery that such HSP60 amplicons can be used as species specific probes or targets for species identification was surprising in view of the widely recognized view that HSP60 is highly conserved at the amino acid level.

The primers and the method of the invention are useful for the identification of organisms, including pathogens and non-pathogens, isolated from human/animal, food, and environmental samples, for example.

BRIEF DESCRIPTION OF THE DRAWINGS

FIGS. 1A–1D show the nucleotide sequences of the 5' (designated as H279) and 3' (designated as H280) flanking region of HSP60 for over 40 different organisms, to which the oligonucleotide primers of the invention hybridize.

FIGS. 4A and 4B show a table of various bacterial isolates utilized for species identification in the method of the invention.

DETAILED DESCRIPTION OF THE INVENTION

Figures 2A, 2B, 3:
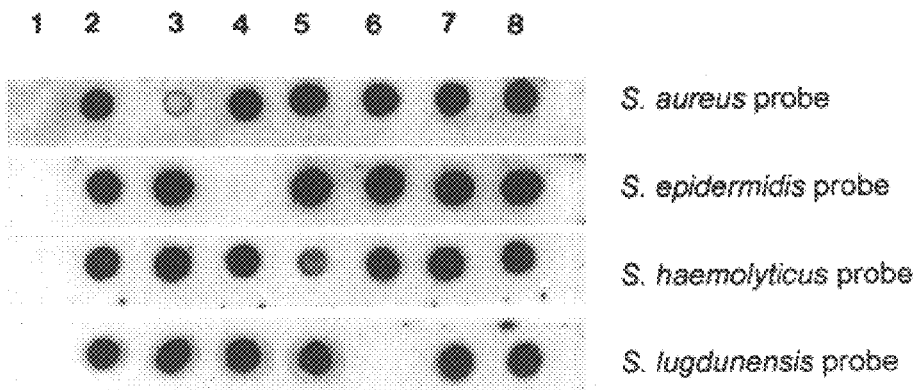
FIGS. 2A and 2B show a dot blot analysis of a mixed genomic DNA PCR/dot blot for species determination. The numbered rows show the species of DNA used for mixed DNA PCR amplification.
FIG. 3 shows a dot blot analysis of bacterial chromosomal DNAs listed in FIG. 4 after hybridization with *S. epidermidis* 9759 (Anthony Chow, University of British Columbia) probe.

The present invention provides oligonucleotide primer(s) for identification of a organism wherein the identification includes amplification of variable regions of a polynucleotide sequence encoding a heat shock protein. The amplicons can be utilized in the method of the invention for identifying and distinguishing organisms at the species level.

In a first embodiment, the present invention provides isolated oligonucleotide primer(s) for identification of an organism wherein the identification includes amplification of a polynucleotide sequence encoding a region of a heat shock protein. The term "isolated" as used herein includes oligonucleotides substantially free of other nucleic acids, proteins, lipids, carbohydrates or other materials with which they may be naturally associated.

As used herein, the term "organism" is meant to include microorganisms (e.g., bacteria), fungi, insects, and any other organism which has the HSP60 gene or its equivalent in its genome. Preferably, the organism is a microorganism and most preferably the microorganism is a prokaryote. Examples of genera of prokaryotes which are useful in the method of the invention include, but are not limited to Staphylococcus, Pseudomonas, Escherichia, Bacillus, Salmonella, Chlamydia, Helicobacter, and Streptococcus and other organisms as listed in FIGS. 1 and 4. Species which can be identified by the method of the invention include for example, *S. haemolyticus, S. epidermidis, S. lugdunensis, S. hominis, E. coli, B. subtilis, Streptococcus faecalis, Bartonella henselae, B. quintana, B. bacilliformis, Yersinia pseudotuberculosis, Vibrio cholera, Legionella pneumophila, Helicobacter pylori, Neisseria gonorrhoeae, Mycobacterium marinum, Candida albicans*, and *P. aeruginosa* as well as organisms listed in FIGS. 1 and 4 herein.

The identification of a species of organism is accomplished by oligonucleotide(s) which are primers for amplification of the highly conserved region of a genomic locus having the sequence of a heat shock protein. These unique oligonucleotide primers were produced based upon identification of the flanking regions contiguous with a region of the heat shock protein, HSP60, locus. These oligonucleotide primers comprise sequences which are capable of hybridizing with the flanking nucleotide sequence having substantially the sequence:

5'-GTTGTCGTACC(G/A)TCACCAGCAATTTC-3' (SEQ ID NO:1) and

5'-AA(G/A)GCGCCTGGTTT(C/T)GGTGAT(C/A)(G/A)(A/T/C/G) (C/A)(G/A)-3' (SEQ ID NO:2), and sequences substantially complementary thereto. The term "sequences substantially complementary thereto" or "substantially the sequence" refers to sequences which hybridize to the sequences provided (e.g., SEQ ID NO:1 and SEQ ID NO:2) under stringent conditions and sequences having sufficient homology with SEQ ID NO:1 and SEQ ID NO:2, such that the oligonucleotide primers of the invention hybridize to the sequence.

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' flanking sequences to hybridize therewith and permit amplification of the genomic locus. By way of example, FIGS. 1A and 1B provide target 5' and 3' flanking sequences for the genomic locus of over 40 different prokaryotic species which are amplified by the primers of the invention. Preferably, the primers of the invention include:

5'-GAIIIIGCIGGIGA(T/C)GGIACIACIAC-3' (SEQ ID NO:3) or

5'-(T/C)(T/G)I(T/C)(T/G)ITCICC(A/G)AAICCIGGIGC(T/C)TT-3' (SEQ ID NO:4), where A is adenosine, T is thymidine, C is cytosine, G is guanosine and I is inosine. Primers having substantial homology to SEQ ID NO:3 and SEQ ID NO:4 are also included in the present invention.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA Polymerase I (Klenow) and nucleotides, results in newly synthesized + and −strands containing the target polymorphic locus sequence. Because these newly synthesized sequences are also templates, repeated cycles of denaturing, primer annealing, and extension results in exponential production of the region (i.e., the target polymorphic locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing the polymorphic locus. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from an organism found in a body sample, such as blood, urine, cerebrospinal fluid, tissue material and the like by a variety of techniques such as that described by Maniatis, et al. (*Molecular Cloning: A Laboratory Manual*, Cold Spring Harbor, N.Y., pp 280, 281, 1982). If the extracted sample is impure (such as plasma, serum, or blood), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffman-Berling (CSH-Quantitative Biology, 43:63, 1978) and techniques for using RecA are reviewed in C. Radding (*Ann. Rev. Genetics,* 16:405–437, 1982).

If the nucleic acid containing the sequence to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be partially complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The newly synthesized polymorphic locus strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleotides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target polymorphic locus nucleic acid sequence to the extent necessary for detection. The amount of the specific nucleic acid sequence produced will accumulate in an exponential fashion.

The amplified product may be detected by analyzing it by Southern blots without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Now that the present invention has provided novel oligonucleotide primers for the amplification of a variable genomic region, the invention provides a method for the identification of the species of an organism comprising amplifying a region of the genomic nucleic acid of the organism by means of oligonucleotide primers which hybridize to target flanking 5' and 3' polynucleotide sequences of the genomic nucleic acid, the target polynucleotide sequence having substantially the sequence selected from the group consisting of:

5'-GTTGTCGTACC(G/A)TCACCAGCAATTTC-3' (SEQ ID NO:1) and

5'-AA(G/A)GCGCCTGGTTT(C/T)GGTGAT(C/A)(G/A)(A/T/C/G) (C/A)(G/A)-3' (SEQ ID NO:2), and sequences substantially complementary thereto, and detecting the amplified region.

Preferably, the method of amplifying is by PCR, as described herein and as is commonly used by those of ordinary skill in the art. Alternative methods of amplification have been described and can also be employed as long as the HSP60 locus amplified by PCR using the primers of the invention is similarly amplified by the alternative means. Such alternative amplification systems include but are not limited to self-sustained sequence replication, 3SR, which begins with a short sequence of RNA of interest and a T7 promoter. Reverse transcriptase copies the RNA into cDNA and degrades the RNA, followed by reverse transcriptase polymerizing a second strand of DNA. Another method nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$-fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair. Nucleic acid amplification by strand displacement activation (SDA) utilizes a short primer containing a recognition site for HincII with a short overhang on the 5' end which binds to target DNA. A DNA polymerase fills in the part of the primer opposite the overhang with sulfur-containing adenine analogs. HincII is added but only cut the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented temperature cycling. Another amplification system useful in the method of the invention is the QB Replicase System. Although PCR is the preferred method of amplification of the invention, these other methods can also be used to amplify the HSP60 locus as described in the method of the invention.

Another embodiment of the invention provides a target genomic polynucleotide locus which is defined by being amplified by the primers of the invention identified by SEQ ID NO:3 and SEQ ID NO:4, or primer sequences substantially complementary thereto, wherein the polynucleotide locus does not hybridize with a polynucleotide locus from *Staphylococcus aureus* amplified by primers of the invention identified by SEQ ID NO:3 and SEQ ID NO:4, or primer sequences substantially complementary thereto. The genomic locus defined by amplification of the primers as described herein encodes a heat shock polypeptide, e.g., HSP60.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise means for amplifying target DNA, said means comprising the necessary enzyme(s) and oligonucleotide primers for amplifying said target DNA from the organism or a cell of the organism. The oligonucleotide primers include primers having a sequence:

5'-GAIIIIGCIGGIGA(T/C)GGIACIACIAC-3' (SEQ ID NO:3) or

5'-(T/C)(T/G)I(T/C)(T/G)ITCICC(A/G)AAICCIGGIGC(T/C)TT-3' (SEQ ID NO:4), or primer sequences substantially complementary thereto. The target flanking 5' and 3' polynucleotide sequence has substantially the sequence selected from the group consisting of:

5'-GTTGTCGTACC(G/A)TCACCAGCAATTTC-3' (SEQ ID NO:1) and

5'-AA(G/A)GCGCCTGGTTT(C/T)GGTGAT(C/A)(G/A)(A/T/C/G)(C/A)(G/A)-3' (SEQ ID NO:2), and sequences substantially complementary thereto.

The following examples are intended to illustrate but not limit the invention. While they are typical of those that might be used, other procedures known to those skilled in the art may alternatively be used.

EXAMPLE 1

Materials and Methods

1. Bacterial Isolates

The bacterial isolates used in the present invention were from the University of British Columbia clinical collection or from Dr. W. Kloos, North Carolina State University, Raleigh, N.C. All cultures were grown in brain heart infusion (BHI) broth followed by streaking on BHI plates to isolate single colonies and for examination of purity and colony characteristics. Other standard methods for bacterial culture will be known to those of skill in the art.

2. Isolation of Genomic DNA

High molecular weight genomic DNA was isolated using the standard SDS/proteinase K, CTAB and phenol/chloroform method (Ausubel, et al., *Current Protocols in Molecular Biology*, Unit 2.4.1.–2.4.2., Greene Publishing Assoc. Inc., J. Wiley and Sons, Inc.). For staphylococci, lysostaphin (Sigma or recombinant product from Applied Microbiology, Inc., New York) was substituted for lysozyme in facilitating cell lysis. DNA concentration was determined by UV spectroscopy, at $A_{260}$ and purity estimated by the $A_{260}/A_{280}$ ratio.

3. PCR Amplification

The following PCR conditions were used: 50 mM KCl, 10 mM Tris, pH 8.3, 1.5 mM $MgCl_2$, 200 µM of each dNTP (all final concentrations), 50 ng of genomic DNA, 2 U of Taq DNA polymerase (GIBCO) and 0.5 µg of each of the degenerate primers H279 (SEQ ID NO:3) and H280 (SEQ ID NO:4). A final volume made up to 100 µl with $dH_2O$ was used.

The sequences of the two primers were 5'-GAIIIIGCIGGIGA(TC)GGIACIACIAC-3' (SEQ ID NO:3) and 5'-(T/C)(T/G)I(T/C)(T/G)ITCICC(A/G)AAICCIGGIGC(T/C)TT-3' (SEQ ID NO:4), for H279 and H280, respectively. Inosine (I) was used to reduce the degeneracy of the primers. The last 26 nucleic acid residues of primers H279 and H280 correspond to DNA residue numbers 688 to 713 and the complement of residue numbers 1267 to 1292, respectively of the *S. epidermidis* HSP 60/10 Genbank submission (accession #U13618). The 5' end sequences of H279 and H280 contain EcoRI and BamHI sites respectively. The thermal cycling conditions were 95° C., for 3' for 1 cycle followed by 40 cycles of 1' at 94° C., 2' at 37° C. and 5' at 72° C. The last cycle was for 10' at 72° C.

Input DNA used in the PCR experiments shown in FIG. 2 were prepared as follows: 50 µl of each overnight culture grown in BHI broth were pooled according to the various combinations shown in FIG. 2. Column 1=no DNA; Column 2=all six species, i.e., all +; Column 3=all minus *S. aureus*; Column 4=all minus *S. epdermidis*; Column 5=all minus *S. haemolyticus*; Column 6=all minus *S. lugdunensis*; Column 7=all minus *S. saprophyticus*; Column 8=all minus *S. schleiferi*. The crude DNA preparations were prepared using the Biorad instagene purification matrix and according to the manufacturers instructions. For the negative DNA control, 300 µl of BHI broth was mock processed. The final extract was in 500 µl of purification matrix and 20 µl of the matrix extract was used as the target DNA for PCR as described above.

10 µl of each reaction following PCR amplification was analyzed on a 2.0% TAE/agarose gel. The DNA fragments were visualized and photographed under UV light following ethidum bromide staining.

4. Purification and Digoxigenin-Labelling of 600 bp HSP 60 PCR Product

The 600 bp PCR products were gel purified after electrophoresis on a 2.0% LMP agarose gel using either beta-agarase I (New England Biolabs) or the QIA Quick Gel Extraction kit (Qiagen, Inc.). The methods were according to the manufacturers protocols. Labelling of the 600 bp fragments for use as probes was carried out using Digoxigenin-11-dUTP and the standard random primer method (Maniatis, et al., supra, Molecular Cloning: A Laboratory Manual; Boehringer Mannheim protocols).

5. Dot Blot/Hybridization of Genomic and PCR Derived DNA with Dig-600 bp HSP 60 Probes For each Staphylococcal isolate, 300 ng of 0.4M NaOH denatured genomic DNA was dot blotted onto nylon membranes (Boehringer Mannheim). For PCR products, the amplified DNA was purified using the QIAquick-spin PCR Purification kit (Qiagen, Inc.). A 1:8000 dilution of the purified PCR product, contained in a 50 µl volume of $dH_2O$ was made and 5 µl of the diluted samples was spotted on the filters. After baking the filters at 120° C. for 30 minutes, the blots were neutralized with 0.5M Tris, pH 7.5, and then dried before use.

The filters were prehybridized at 42° C. in 50% formamide, 5X SSC, 2% Boehringer Mannheim blocking reagent, 0.1% N-lauryl sarcosine and 0.02% sodium dodecyl sulphate (SDS) for at least 1 hour. Hybridization with the same prehybridization buffer and dig-probes at 40–50 ng/ml was allowed to proceed overnight at 42° C. The filters were washed sequentially after hybridization with 2xSSC/0.1% (w/v) SDS; 2x15' at room temperature followed by 2x15' washes at 68° C. with 0.1X SSC/0.1% (w/v) SDS. Chemiluminescent detection was as described in the Boehringer Mannheim protocols.

EXAMPLE 2

Identification of Bacterial Isolates by HSP60 Amplification

Genomic DNA from 58 bacterial isolates representing 29 species and 2 subspecies of the Staphylococci and three other genera (*E. coli, P. aeruginosa* and *B. subtilis*) were tested against 600 bp HSP 60 probes from *S. aureus* (8325-4). *S. epidermidis* (9759), *S. haemolyticus* (ATCC 29970, American Type Culture Collection, Rockville, Md.), *S. lugdunensis* (DRSN 850412), *S. saprophyticus* (KL 122) and *S. schleiferi* (ATCC 43808) by dot blot analysis. From the results of the dot blot experiments (FIG. 3), four false positives and three false negatives were identified. (In FIG. 4, all isolates marked with an asterisk were obtained from Dr. W. Kloos, N. Carolina State University. All others were from the in-house collection at University of British Columbia.)

FIG. 3 shows an example of the dot blot results obtained when 58 DNA isolates were probed with one of the above six Staphylococcal species probes. The *S. epidermidis* probe exhibited 100% sensitivity (FIGS. 3 and 4), correctly picking-up for the four *S. epidermidis* isolates. But three false positives identified as *S. epidermidis* were *S. haemolyticus* (8459), *S. saphrophyticus* (9761) and *S. hominis* (8458). The *S. aureus* probe identified all 6 *S. aureus* samples while only one false positive, *S. sciuri*, was identified. Further analysis of the results in FIG. 4 shows that the *S. haemolyticus* probe correctly identified 2 of the 4 *S. haemolyticus* isolates. A false positive (*S. capitis* 8468) was also encountered with the *S. haemolyticus* probe. The *S. schleiferi* probe gave 100% sensitivity and specificity, picking-up both isolates and also a subspecies, *S. schleiferi* subspecies *coagulans*; ATCC 49545. The *S. saprophyticus* probe correctly identified three of the four *S. saprophyticus* isolates, while the fourth *S. saprophyticus* 9761, gave a false negative result. Finally, the *S. lugdunensis* probe correctly identified the lone homologous isolate. However, two false positives were identified, namely *S. haemolyticus* (8564) and *S. xylosus* (8584). All of the false positives and negatives were clinical isolates accumulated over many years from various sources. Interestingly, each of the seven misidentified isolates were picked-up by one of the six probes used (FIG. 4). The same culture plates from which the original seven DNA samples were derived from were used to provide isolates which were sent to the British Columbia Centres for Disease Control for speciation by phenotypic methods. The results from Table 1 confirm that all six HSP 60 probes were able to correctly identify all of the 58 bacterial isolates with 100% sensitivity and specificity. A plausible explanation for the false positives and negatives may be that these isolates were originally misidentified.

TABLE 1

SPECIATION ANALYSIS OF FALSE POSITIVE AND NEGATIVE ISOLATES BY COMPARISON WITH HSP60 PROBE IDENTIFICATION AND PHENOTYPE ANALYSIS

| Isolate Previously Identified[a] | Isolate Identified by HSP60 Probes[b] | Isolate Identified by Phenotyping[c] |
|---|---|---|
| 1) *S. saprophyticus* 9761 (FN) | *S. epidermidis* | *S. epidermidis* |
| 2) *S. hominis* 8458 (FP) | *S. epidermidis* | *S. epidermidis* |
| 3) *S. sciuri* 10034 (FP) | *S. aureus* | *S. aureus* |
| 4) *S. capitis* 8468 (FP) | *S. haemolyticus* | *S. haemolyticus* |
| 5) *S. haemolyticus* 8459 (FN) | *S. epidermidis* | *S. epidermidis* |
| 6) *S. xylosus* 8584 (FP) | *S. lugdunensis* | *S. lugdunensis* |
| 7) *S. haemolyticus* 8589 (FN) | *S. lugdunensis* | *S. lugdunensis* |

[a]Previously identified from UBC collection
[b]Data as from FIG. 4
[c]Phenotyping carried out at The Provincial Laboratory, B.C. Centres for Disease Control, Vancouver, British Columbia, Canada.
(FP) = false positive
(FN) = false negative FIG. 2 shows the results of experiments used to determine (i) if the degenerate primers could be used to amplify specific Staphylococcal targets from mixed cultures and (ii) if species specific HSP 60 probes identify the correct target from mixed species PCR products. Probes for the four species chosen represent some of the most common Staphylococcal human pathogens. In all cases, when the four respective probes were used, good specificity was observed. Some residual background signal was observed in the blots hybridized with the *S. haemolyticus* and *S. aureus* probes, though the signal to noise ratio is high.

SUMMARY

Based on the hybridization results of the 58 bacterial isolates tested as described herein, genomic sequences of HSP60 genes are shown to be useful targets for species identification. The ubiquitous presence of such genes in both procaryotes and eucaryotes makes HSP60 an even more attractive target (Yura, and More, supra; Ellis and van der Vies, supra; Gething and Sambrook, supra; Craig, et al., supra).

The degenerate primers of the invention were capable of amplifying a 600 bp putative HSP 60 fragment from all Staphylococci species and subspecies listed in FIG. 4. Thus, species specific probes can be easily generated with such primers. The Examples presented herein concentrated specifically on six species responsible for the majority of clinical Staphylococcal infections (Kloos and Lamba, supra). The initial genomic DNA dot blot data (FIGS. 2, 4) generated a total of seven Staphylococcal false positives and negatives when the six probes were tested sequentially on the 58 bacterial isolates. All of those seven isolates, like the rest of the University of British Columbia culture collection have been derived from diverse sources over many years. The results of the new phenotype identification of these seven isolates (Table 1) carried out by another laboratory concurs with those of the HSP 60 DNA dot blot data (FIGS. 2, 4). DNA from three other genera represented by *E. coli*, *P. aeruginosa* and *B. subtilis* did not hybridize to any of the six Staphylococcal probes (FIG. 4).

The PCR dot blot results (FIG. 2) illustrate the potential utility of the method of the invention for identification of Staphylococci via HSP60 target sequences, even in mixed cultures. Such a PCR coupled method is useful for detection of specific targeted organisms in clinical samples, especially those from normally sterile sites such as cerebrospinal fluid and sera. The degenerate PCR primers have been used successfully as illustrated herein, to amplify the expected 600 bp HSP 60 fragment from diverse organisms. Though the HSP60 family of proteins are highly conserved (Ellis and van der Vies, supra; Gething and Sambrook, supra), the present invention shows that there is sufficient DNA variation between species in the target region used in the present invention to be useful for species identification.

Although the invention has been described with reference to the presently preferred embodiment, it should be understood that various modifications can be made without departing from the spirit of the invention. Accordingly, the invention is limited only by the following claims.

What is claimed is:

1. A method for identification of a species of an organism comprising:
   a) amplifying a region of a genomic nucleic acid of the organism by means of oligonucleotide primers which hybridize to target flanking 5' and 3' polynucleotide sequences of the genomic nucleic acid, the target polynucleotide sequence having the sequence selected from the group consisting of:
   5'-GTTGTCGTACC(G/A)TCACCAGAATTTC-3' (SEQ ID NO:1) and 5'-AA(G/A)GCGCCTGGTTT(C/T)GGTGAT(C/A)(G/A)(A/T/C/G) (C/A)(G/A)-3' (SEQ ID NO:2), and sequences complementary thereto; and
   b) detecting the amplified region; and
   c) identifying the species of the organism.

2. The method of claim 1, wherein the amplifying is by polymerase chain reaction (PCR).

3. The method of claim 1, wherein the primer is 5'-GAIIIIGCIGGIGA(T/C)GGIACIACIAC-3' (SEQ ID NO:3) or 5'-(T/C)(T/G)I(T/C)(T/G)ITCICC(A/G)AAICCIGGIGC(T/C)TT-3' (SEQ ED NO:4).

4. The method of claim 3, wherein the organism is a microorganism.

5. The method of claim 4, wherein the organism is a prokaryote.

6. The method of claim 5, wherein the prokaryote is a member of a genus is selected from the group consisting of Staphylococcus, Pseudomonas, Escherichia, Bacillus, Salmonella, and Streptococcus.

7. The method of claim 6, wherein the species of the genus is selected from the group consisting of *S. aureus, S. haemolyticus, S. epidermidis, S. lugdunensis, S. hominis, E. coli, B. subtilis,* and *P. aeruginosa.*

* * * * *